United States Patent [19]

Massie

[11] B  3,992,453
[45] Nov. 16, 1976

[54] HYDROFORMYLATION PROCESS
[75] Inventor: Stephen N. Massie, Palatine, Ill.
[73] Assignee: Universal Oil Products Company, Des Plaines, Ill.
[22] Filed: May 22, 1974
[21] Appl. No.: 472,241
[44] Published under the second Trial Voluntary Protest Program on February 17, 1976 as document No. B 472,241.

[52] U.S. Cl. .................... 260/604 HF; 260/632 HF
[51] Int. Cl.² .................... C07C 45/08; C07C 29/02
[58] Field of Search ................ 260/604 HF, 632 HF

[56] References Cited
UNITED STATES PATENTS
3,511,880  5/1970  Booth .......................... 260/604 HF
3,555,098  1/1971  Olivier et al. ................. 260/604 HF
3,641,076  2/1972  Booth .......................... 260/604 HF Primary Examiner—James O. Thomas, Jr.
Assistant Examiner—James H. Reamer
Attorney, Agent, or Firm—James R. Hoatson, Jr.; Raymond H. Nelson; William H. Page, II

[57] ABSTRACT

A hydroformylation process comprising the treatment of an unsaturated compound with carbon monoxide and hydrogen in the presence of a catalyst comprising a cobalt-containing compound is improved by the addition of a promoter comprising an ester of carbonic acid.

13 Claims, No Drawings

HYDROFORMYLATION PROCESS

This invention relates to a process for the preparation of alcohols and aldehydes from the treatment of unsaturated compounds. More specifically, this invention relates to a process for the production of alcohols and aldehydes which comprises the treatment of an unsaturated compound with carbon monoxide and hydrogen in the presence of a catalyst comprising a cobalt-containing compound, said process being improved by the addition of a promoter comprising an ester of carbonic acid.

Processes directed to the production of reaction mixtures comprising substantial amounts of aldehydes and alcohols by the hydroformylation of unsaturated compounds with carbon monoxide and hydrogen in the presence of certain catalysts are well-known in the art. The aldehydes and alcohols produced generally correspond to the compounds obtained by the addition of a carbonyl or carbinol group to an olefinically unsaturated carbon atom in the starting material with simultaneous saturation of the olefin bond. The process is known as hydroformylation and involves a reaction which may be shown by the general generic formula:

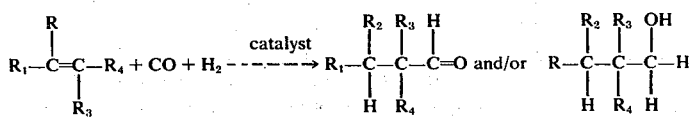

where $R_1$, $R_2$, $R_3$ and $R_4$ may be chosen from a group comprising an organic, halide or hydrogen radical.

It has been shown in the prior art that dicobalt octacarbonyl has generally been used as a catalyst for the hydroformylation of unsaturated compounds. This catalyst, which can be prepared from many forms of cobalt, usually decomposes rapidly at elevated temperatures unless high pressures of about 200–4500 pounds per square inch guage of carbon monoxide are maintained, depending on the temperature. Correspondingly, high pressures of hydrogen are also necessary. Another serious disadvantage of hydroformylation processes has been the necessity of proceeding in two steps when alcohols are the desired products. Another disadvantage inherent in the hydroformylation process is the relative inability to direct the reactions involved to the production of predominantly terminal alcohols when the olefins contain more than 2 carbon atoms, particularly when the charge stock to the process comprises primarily internal olefins. Still another and more basic problem in a hydroformylation reaction is the production of alkanes which comprise an almost worthless by-product of the hydroformylation reaction.

In contradistinction to the prior art, it has now been shown that the utilization of a promoter comprising an ester of carbonic acid, which is present in the hydroformylation of an unsaturated compound by carbon monoxide and hydrogen in the presence of a catalyst comprising a cobalt-containing compound, will greatly increase the quantity of terminal alcohols and aldehydes which are the desired products of the hydroformylation reaction and will not increase the quantity of alkanes produced in said hydroformylation reaction. The utilization of the present invention will allow the manufacturers a greater control of linear selectivity of products (the term "linear selectivity" as defined in the specification and the appended claims will refer to the mathematical percentage relationship of the mols of straight-chain oxygenated product divided by the mols of total oxygenated product multiplied by 100). The utilization of the present invention will also allow the manufacturer to reduce his costs of production and thereby eventually reduce the cost of the alcohols and aldehydes to the consumer. The invention will also allow the manufacturer to perform more efficient hydroformylation processes without any excess problems of greater alkane formation.

The desired products to the process of this invention, namely alcohols and aldehydes, are utilized in the chemical industry in many ways. For example, alcohols are utilized in the synthesis of other organic derivatives; as solvents; as an extraction medium; in dyes; synthetic drugs; synthetic rubber; detergents; cleaning solutions; surface coatings; cosmetics; pharmaceuticals; in the preparation of esters; as a solvent for resin in coatings; as a plasticizer; dyeing assistant; hydraulic fluids; detergent formulations; dehydrating agents; or the use of aldehydes as exemplified by their utility as perfumeries, or in the synthesis of primary alcohols.

It is therefore an object of this invention to provide a process for the preparation of aldehydes and alcohols.

A further object of this invention is to provide an improvement in a process for the preparation of alcohols and aldehydes utilizing certain promoter compositions of matter which will permit the recovery of the desired compounds in a more economically feasible manner.

In one aspect an embodiment of this invention resides in a method for the hydroformylation of an unsaturated compound which comprises reacting said unsaturated compound with carbon monoxide and hydrogen in the presence of a catalyst comprising a cobalt-containing compound at hydroformylation conditions and recovering the resultant hydroformylation product, the improvement which consists in effecting the hydroformylation in the presence of a promoter comprising an ester of carbonic acid.

A specific embodiment of this invention resides in a process for preparing undecanol-1 which comprises hydroformylating decene-5 with carbon monoxide and hydrogen in the presence of dicobalt octacarbonyl and a promoter comprising diethyl carbonate at a temperature of 180°C and a pressure of 120 atmospheres of hydrogen and 120 atmospheres of carbon monoxide, and recovering the resultant undecanol-1.

Another specific embodiment of this invention resides in a process for preparing a mixture of dodecanol-1, 2-methylundecanol-1, 2-ethyldodecanol-1, 2-propylnonanol-1, tridecanol-1, 2-methyldodecanol-1, 2-ethylundecanol-1, tetradecanol-1, 2-methyltridecanol-1, 2-ethyldodecanol-1, pentadecanol-1, 2-methyltetradecanol-1, and 2-ethyltridecanol-1 which comprises the treatment of a mixture of undecene-5, dodecene-4, tridecene-6 and tetradecene-4 in the presence of a catalyst comprising dicobalt octacarbonyl and a promoter comprising ethylene carbonate at a temperature of 125°C and a pressure of 120 atmospheres of hydrogen and 30 atmospheres of carbon monoxide and recovering the resultant mixture of dodecanol-1, 2-methylundecanol-1, 2-ethyldecanol-1, 2-propylnonanol-1, tridecanol-1, 2-methyldodecanol-1, 2-ethylundecanol-1, tetradecanol-1, 2-methyltridecanol-1, 2-ethyldodecanol-1, pentadecanol-1, 2-methyltetradecanol-1, and 2-ethyltridecanol-1.

Other objects and embodiments will be found in the following further detailed description of the present invention.

As hereinbefore set forth the present invention is concerned with a process for preparing alcohols and aldehydes, said process being effected by the hydroformylation of an unsaturated compound with carbon monoxide and hydrogen in the presence of a catalyst comprising a cobalt-containing compound and a promoter comprising an ester of carbonic acid. The reaction is effected under conditions which include a temperature in the range of from about 75°C to about 300°C and preferably in a range of from about 100°C to about 200°C. In addition, another reaction condition involves pressure, said pressure ranging from atmospheric up to 500 atmospheres or more. When superatmospheric pressures are employed said pressure is afforded by the introduction of gaseous carbon monoxide, hydrogen and, if desired, any substantially inert gas such as nitrogen or helium may also be charged to the reaction zone.

Examples of suitable unsaturated compounds which are utilized as the starting material in the hydroformylation process of this invention include, in particular, propylene, butene-1, butene-2, isobutene, pentene-1, pentene-2, 2-methylbutene-1, 2-methylbutene-2, hexene-1, 3-methylpentene-1, 2-methylpentene-2, heptene-2, 2-methylhexene-2, 3-methylhexene-2, octene-1, octene-2, 3-methylheptene-1, 2-methylheptene-2, nonene-3, 3-methyloctene-2, decene-2, decene-5, 3,4-dimethyloctene-2, 4-ethyloctene-2, undecene-3, undecene-4, 4-methyldecene-2, 4,5-dimethylnonene-2, dodecene-3, tridecene-2, tetradecene-3, pentadecene-5, heptene-1, nonene-1, decene-1, decene-2, decene-3, decene-4, decene-5, undecene-1, undecene-2, undecene-3, undecene-4, undecene-5, dodecene-1, dodecene-3, dodecene-5, tridecene-1, tridecene-3, tridecene-4, tridecene-6, tetradecene-1, tetradecene-7, pentadecene-1, pentadecene-4, pentadecene-6, 2-methoxybutene-2, 2-methoxypentene-1, 2-ethoxyhexene-1, 1-propoxyheptane, 2-ethoxyoctene-1, 2,3-diethoxyundecene-3, 1-chlorobutene-2, 2-chloropentene-1, 2-bromohexene-2, 2,3-dichlorooctene-1, 3-iodooctene-2, 2-methoxy-3-chlorodecene-2, 3,4-dimethyl-2-chlorooctene-2, cyclopentene, cyclohexene, cycloheptene, cyclooctene, cyclononene, cyclodecene, 1-methylcyclohexene-1, 1-ethylcyclohexene-1, 2,3-dipropycycloheptene-1, 1-methoxycyclopentene-1, 2,3-dipropycycloheptene-1, 1-chlorocycloheptene-1, 2,3,4-trichlorocyclooctene-1, or mixtures of linear internal olefins such as internal olefins possessing carbon numbers of 11 through 14 or 15 through 18, etc.

The catalytic compositions of matter which are used in the process of this invention comprise any known hydroformylation cobalt-containing catalyst such as dicobalt octacarbonyl. It is also contemplated within the scope of this invention that a phosphorous-containing ligand such as a trialkyl phosphine may be present as one component of the complex cobalt catalyst. The hydrocarbonyl components need not necessarily be the same, and suitable tertiary organo phosphine ligands comprise the mixed phosphine wherein different members of the group are comprised of alkyls, aryls, aralkyls, and alkaryls. Preferred catalysts of the above-defined class comprise those wherein the hydrocarbonyl component contains from about 1 to about 20 carbon atoms and the total number of carbons in the tertiary organo phosphine group does not exceed about 30. A particularly preferred group of catalysts within the above-defined trialkyl phosphine-cobalt carbonyl complexes is one in which the component of the catalyst is a trialkyl phosphine in which each alkyl is a lower alkyl having from 1 to about 10 carbon atoms. Specific examples of suitable catalysts of the above-defined class comprise complexes between cobalt, carbon monoxide and one of the following tertiary organo phosphines such as trimethylphosphine, triethylphosphine, tris-n-butylphosphine, triamylphosphine, trihexylphosphine, tripropylphosphine, trinonylphosphine, tridecylphosphine, tri-n-butyloctadecylphosphine, dimethylethylphosphine, diamylethylphosphine, ethyl-bis-($\beta$-phenylethyl)phosphine, dimethylcyclopentylphosphine, diphenylbenzylphosphine, diethylphenylphosphine, etc. It should be noted that the presence of the organo phosphine is not critical to the above set forth invention and that the promoter comprising the carbonic acid can function in the sole presence of the cobalt-containing compound catalyst. It is also within the scope of this invention to charge a cobalt-containing compound which will generate dicobalt octacarbonyl or hydridocobalt tetracarbonyl under the reaction conditions, said compounds being exemplified by cobalt carbonate, cobalt octanate, cobalt naphthenate, cobalt chloride, etc.

In the very essence of this invention it is contemplated that the hydroformylation reaction may be effected in the presence of a promoter comprising an ester of carbonic acid, said presence of the ester of the carbonic acid creating a greater linear selectivity which is defined as the mathematical percentage relationship of the moles of the straight-chain oxygenated product divided by the moles of total oxygenated product multiplied by 100. The esters of carbonic acid are exemplified by ethylene carbonate, propylene carbonate, diethyl carbonate, dipropyl carbonate, dibutyl carbonate, dipentyl carbonate, dihexyl carbonate diheptyl carbonate, dioctyl carbonate, di-2-ethyl-1-hexyl carbonate, dinonyl carbonate, didecyl carbonate, ditetradecyl carbonate, dinonyldecyl carbonate, ethyl propyl carbonate, ethyl butyl carbonate, ethyl pentyl carbonate, ethyl hexyl carbonate, ethyl heptyl carbonate, ethyl octyl carbonate, ethyl nonyl carbonate, ethyl decyl carbonate, propyl butyl carbonate, propyl pentyl carbonate, propyl hexyl carbonate, propyl heptyl carbonate, propyl octyl carbonate, propyl nonyl carbonate, propyl decyl carbonate, butyl pentyl carbonate, butyl hexyl carbonate, butyl heptyl carbonate, butyl octyl carbonate, butyl nonyl carbonate, butyl decyl carbonate, pentyl hexyl carbonate, pentyl heptyl carbonate, pentyl octyl carbonate, pentyl nonyl carbonate, pentyl decyl carbonate, hexyl heptyl carbonate, hexyl octyl carbonate, hexyl decyl carbonate, heptyl octyl carbonate, heptyl nonyl carbonate, heptyl decyl carbonate, octyl nonyl carbonate, octyl decyl carbonate, nonyl decyl carbonate, diphenyl carbonate, phenyl ethyl carbonate, phenyl propyl carbonate, phenyl butyl carbonate, phenyl pentyl carbonate, phenyl hexyl carbonate, phenyl heptyl carbonate, phenyl nonyl carbonate, phenyl octyl carbonate, phenyl decyl carbonate, di-2- tolyl carbonate, di-2,3-xlyl carbonate, 2-ethyl(phenyl) 2-tolyl carbonate, dinaphthyl carbonate, etc. It is also contemplated within the scope of this invention that esters of chloroformic(chlorocarbonic) acid may also be used as a promoter of this invention but not necessarily with equivalent results.

It is contemplated within the scope of the process of the present invention that the hydroformylation may be effected in an inert organic media as exemplified by n-pentane, n-hexane, n-heptane, n-octane, n-nonane, isooctane (2,2,4-trimethylpentane), cyclohexane, methylcyclohexane, benzene, toluene, etc.

It is understood that the aforementioned cobalt-containing compound catalysts, unsaturated compounds, esters of carbonic acid and inert organic media are only representative of the class of compounds which may be employed, and that the present invention is not necessarily limited thereto.

The process of this invention may be effected in any suitable manner and may comprise either a batch or a continuous type operation. For example when a batch type operation is employed the reactants comprising the unsaturated compounds, carbon monoxide and hydrogen are placed in an appropriate apparatus along with a catalyst comprising a cobalt-containing compound and a promoter comprising an ester of carbonic acid. The autoclave is sealed, heated to a desired operating temperature and maintained thereat for a predetermined residence time. At the end of this time, which may comprise from about 0.5 up to 50 hours or more in duration, the heating is discontinued, the autoclave is allowed to return to room temperature and the autoclave is vented thereby allowing it to return to ambient temperature. The reaction mixture is then recovered, separated from the catalyst and promoter and subjected to conventional means of purification and separation, said means includes washing, drying, extraction, evaporation, fractional distillation, etc. whereby the desired alcohol, aldehyde or alcohol-aldehyde mixture is recovered.

It is also contemplated within the scope of this invention that the hydroformylation process for obtaining the desired alcohols and aldehydes may be effected in a continuous manner of operation. When such a type of operation is employed, the reactants comprising the unsaturated compounds are continuously charged to the hydroformylation zone containing the cobalt-containing compound and a promoter comprising an ester of carbonic acid, said hydroformylation zone being maintained at the proper operating conditions of temperature and pressure by heat and the admission of the requisite quantities of carbon monoxide, hydrogen and any substantially inert gas as required for effecting of the hydroformylation reaction. After completion of the desired residence time, the reactor effluent is continuously withdrawn and subjected to conventional means of separation whereby the desired alcohol or aldehyde is recovered while any ester of carbonic acid and unreacted starting material comprising the unreacted, unsaturated compound, carbon monoxide or hydrogen are recycled to the reaction zone to form a portion of the feedstock or a gaseous hydrogen or carbon monoxide stream. The cobalt values may be recovered from the reaction mixture by various methods known to the art and regenerated to form fresh catalysts.

Examples of alcohols and aldehydes which may be prepared according to the process of this invention will include butanol-1, pentanol-1, hexanol-1, heptanol-1, octanol-1, nonanol-1, decanol-1, 2-methylbutanol-1, 2-methylpentanol-1, 2-ethylpentanol-1, 2-methylhexanol-1, 2-ethylhexanol-1, 2-chloropropanol-1, 3-chlorohexanol-1, 2,3-dichloroheptanol-1, 2-ethyl-3-chlorooctanol-1, butanal, pentanal, hexanal, heptanal, octanal, nonanal, decanal, undecanal, 2-methylbutanal, 2-methyloctanal, cyclopentyl carbinol, cyclohexyl carbinol, cycloheptylcarbinol, cyclooctyl carbinol, cyclononyl carbinol, cyclodecyl carbinol, mixed hydroxymethylalkanes, mixed formylalkanes, etc.

The following examples are given to illustrate the process of the present invention which, however, are not intended to limit the generally broad scope of the present invention in strict accordance therewith.

EXAMPLE I

In this example 143.0 millimoles of decene-5 was added to an 850 milliliter glass-lined rotating autoclave containing 1.0 millimole of dicobalt octacarbonyl and 4.0 millimoles of diethyl carbonate in 5 milliliters of n-pentane, said autoclave being equipped with heating and pressure attainment devices. The rotating autoclave was sealed, pressurized by the entry of 120 atmospheres of carbon monoxide and 120 atmospheres of hydrogen, heated to a temperature of 180°C., and maintained thereat for a period of time comprising 1 hour. At the end of the 1 hour period of time, the heating was terminated thereby allowing the rotating autoclave to return to room temperature and the carbon monoxide and hydrogen were carefully vented thereby allowing said autoclave to return to ambient pressure. At this point, the product was removed from the glasslined rotating autoclave and analyzed by means of gas-liquid chromatographic instrumentation, said analysis disclosed the product to be undecanol-1 with a performance factor of 1.10 and a mixture of 2-methyldecanol-1 and 2-ethylnonanol-1 plus minor quantities of the corresponding aldehydes. The term "performance factor" symbolizes the mathematical relationship of the linear selectivity of the system of Example I utilizing a promoter comprising the ester of carbonic acid, diethyl carbonate, divided by the linear selectivity of a former standardized system which duplicated Example I with the absence of the promoter comprising the ester of carbonic acid, diethyl carbonate. The term linear selectivity was hereinafter defined as the mathematical relationship of the mols of straight-chain oxygenated product divided by the mols total of oxygenated product multiplied by 100. The unsaturated compound was found to be 97.0 percent converted to the oxygenated product while the percentage of alkane product, decane, was held to 2 percent.

It should be noted that the performance factor of 1.10 of Example I demonstrates that the presence of the diethyl carbonate promoter increased the amount of terminal hydroformylation products produced as compared to a set of identical standardized conditions in which the promoter was not utilized.

EXAMPLE II

In this example 143.0 millimoles of decene-5 was added to an 850 milliliter glass-lined rotating autoclave containing 1.0 millimoles of dicobalt octacarbonyl and 4.0 millimoles of ethylene carbonate and 5 milliliters of n-pentane, said autoclave being equipped with heating and pressure attainment devices. The rotating autoclave was sealed, pressurized by the entry of 120 atmospheres of carbon monoxide and 120 atmospheres of hydrogen, heated to a temperature of 180°C., and maintained thereat for a period of time comprising 1 hour. At the end of the 1 hour period of time, the heating was terminated thereby allowing the rotating autoclave to return to room temperature and the carbon monoxide and hydrogen were carefully vented thereby allowing said autoclave to return to ambient pressure. At this point, the product was removed from the glass-lined rotating autoclave and analyzed by means of gas-liquid chromatographic instrumentation, said analysis disclosed the product to be undecanol-1 with a performance factor of 1.10 and a mixture of 2-methyldecanol-1 and 2-ethylnonal-1 plus minor quantities of the corresponding aldehydes. The term "performance factor" symbolizes the mathematical relationship of the linear selectivity of the system of Example II utilizing a promoter comprising an ester of carbonic acid, ethylene carbonate, divided by the linear selectivity of the former standardized system which duplicated Example II with the absence of the promoter comprising an ester of a carbonic acid, ethylene carbonate. The term linear selectivity was hereinbefore defined as a mathematical relationship of the moles of straight-chained oxygenated products divided by the moles total of oxygenated product multiplied by 100 percent. The unsaturated compound was found to be nearly quantitively converted while the percentage of alkane product, mostly decane, was held to 2 percent.

It should be noted that the performance factor of 1.10 of Example II demonstrates that the presence of the ethylene carbonate promoter increased the amount of terminal hydroformylation products produced as compared to a set of identical standard experiments in which the ethylene carbonate promoter was not utilized.

EXAMPLE III

In this example 100.0 millimoles of tetradecene-7 are placed in an 850 milliliter rotating autoclave containing 0.5 millimoles of a catalyst comprising a complex between cobalt, carbon monoxide and diethylphenylphosphine and 1.0 millimoles of diphenyl carbonate in 50 milliliters of cyclohexane, said autoclave being equipped with a device for heating and pressure attainment. The rotating autoclave is heated to a temperature of 200°C, after being pressurized with 100 atmospheres of hydrogen and 100 atmospheres of carbon monoxide and maintained thereat for a period of time comprising 2 hours. At the end of the 2 hour period of time, the heating is terminated, thereby allowing the rotating autoclave to return to room temperature and the rotating autoclave is vented, thereby allowing the rotating autoclave to return to ambient pressure. At this point the product is removed from the rotating autoclave and analyzed by means of gas-liquid chromotographic instrumentation, said analysis disclosing the product to be a mixture of pentadecanol-1, 2-methyltetradecanol-1 and 2-ethyltridecanol-1 possessing more of the terminal hydroformylation products than is normally obtained in a similar hydroformylation reaction when an ester of carbonic acid, namely, diphenyl carbonate, had not been utilized.

EXAMPLE IV

In this example 125.0 millimoles of octene-3 are placed in an 850 milliliter rotating autoclave containing 0.5 millimoles of dicobalt octacarbonyl, 1.0 millimoles of dioctyl carbonate and 50 milliliters of benzene, said autoclave being equipped with a device for heating and pressure attainment. The rotating autoclave is heated to a temperature of 250°C, after being pressurized with 75 atmospheres of hydrogen and 50 atmospheres of carbon monoxide and maintained thereat for a period of time comprising 6 hours. At the end of the 6 hour period of time, the heating is terminated thereby allowing the rotating autoclave to return to room temperature, and the rotating autoclave is vented, thereby allowing the rotating autoclave to return to ambient pressure. At this point, the product is removed from the rotating autoclave and analyzed by means of gas-liquid chromatographic instrumentation, said analysis disclosing the product to be a mixture of nonanol-1, 2-methyloctanol-1 and 2-ethylheptanol-1 possessing more terminal hydroformylation products than is normally obtained in a similar hydroformylation reaction when an ester of carbonic acid, namely, dioctyl carbonate, had not been utilized.

EXAMPLE V

In this example 95.0 millimoles of condensed pentene-2 are placed in an 850 milliliter rotating autoclave containing 0.5 millimoles of dicobalt octacarbonyl, 1.0 millimoles of octyl pentyl carbonate and 50 milliliters of isooctane(2,2,4-trimethylpentane), said autoclave being equipped with a device for heating and pressure attainment. The rotating autoclave is heated to a temperature of 275°C after being pressurized with 50 atmospheres of hydrogen and 75 atmospheres of carbon monoxide and maintained thereat for a period of time comprising 1 hour. At the end of the 1 hour period of time the heating is terminated, thereby allowing the rotating autoclave to return to room temperature, and the rotating autoclave is vented, thereby allowing the rotating autoclave to return to ambient pressure. At this point the product is removed from the rotating autoclave and analyzed by means of gas-liquid chromatography instrumentation, said analysis disclosing the product to be predominantly a mixture of hexanol-1, 2-methylpentanol-1 and 2-ethylbutanol-1 possessing more of the terminal hydroformylation products than is normally obtained in a similar hydroformylation reaction when an ester of carbonic acid, namely, octyl pentyl carbonate, had been utilized.

EXAMPLE VI

In this example 110.0 millimoles of hexadecene-8 are placed in an 850 milliliter rotating autoclave containing 0.5 millimoles of a catalyst comprising dicobalt octacarbonyl, 1.1 millimoles of ethylene carbonate and 50 milliliters of cyclohexane, said autoclave being equipped with a device for heating and pressure attainment. The rotating autoclave is heated to a temperature of 110°C, after being pressurized with 100 atmospheres of hydrogen and 100 atmospheres of carbon monoxide and maintained thereat for a period of time comprising 2 hours. At the end of the 2 hour period of time, the heating is terminated, thereby allowing the rotating autoclave to return to room temperature and the rotating autoclave is vented, thereby allowing the rotating autoclave to return to ambient pressure. At this point the product is removed from the rotating autoclave and analyzed by means of gas-liquid chromatography instrumentation, said analysis disclosing the product to be predominantly a mixture of heptadecanal-1, 2-methylpentadecanal-1, and 2-ethyltetradecanal-1 possessing more of the terminal hydroformylation products than is normally obtained in a similar hydroformylation reaction when an ester of carbonic acid, namely, ethylene carbonate, had not been utilized.

EXAMPLE VII

In this example 100.0 millimoles of a mixture comprising undecene-5, dodecene-4, tridecene-6 and tetradecene-4 are placed in an 850 milliliter rotating autoclave containing 1.0 millimoles of a catalyst comprising dicobalt octacarbonyl, 1.0 millimoles of diethyl carbonate and 50 milliliters of n-pentane, said autoclave being equipped with a device for heating and pressure attainment. The rotating autoclave is heated to a temperature of 175°C, after being pressurized with 150 atmospheres of hydrogen and 150 atmospheres of carbon monoxide and maintained thereat for a period of time comprising 3 hours. At the end of the 3 hour period of time, the heating is terminated, thereby allowing the rotating autoclave to return to room temperature and the rotating autoclave is vented, thereby allowing the rotating autoclave to return to ambient pressure. At this point the product is removed from the rotating autoclave and is analyzed by means of gas-liquid chromatographic instrumentation, said analysis disclosing the product to be a mixture of dodecanol-1, 2-methylundecanol-1, 2-ethyldecanol-1, 2-propylnonanol-1, tridecanol-1, 2-methyldodecanol-1, 2-ethylundecanol-1, tetradecanol-1, 2-methyltridecanol-1, 2-ethyldodecanol-1, pentadecanol-1, 2-methyltetradecanol-1, and 2-ethyltridecanol-1 possessing more of the terminal hydroformylation products than is normally obtained in a similar hydroformylation reaction when an ester of carbonic acid, namely, diethyl carbonate, had not been utilized.

I claim as my invention:

1. In a method for the hydroformylation of an unsaturated compound which comprises reacting a $C_1$ to $C_{15}$ alkene with carbon monoxide and hydrogen in the presence of a catalyst comprising cobalt hydrocarbonyl wherein the hydrocarbonyl contains from about 1 to about 20 carbon atoms or a complex between cobalt, carbon monoxide and a tertiary organo phosphine wherein the number of carbons in the tertiary organo phosphine group does not exceed 30 at a temperature in the range of from about 75°C to about 300°C, and a pressure of from about 1 atmosphere to about 500 atmospheres, and recovering the resultant hydroformylation product, the improvement which consists in effecting the hydroformylation in the presence of a promoter comprising an ester of carbonic acid selected from the group consisting of ethylene carbonate, propylene carbonate, diphenyl carbonate, dialkyl carbonate wherein the alkyl groups contain from 2 to 10 carbon atoms and phenyl alkyl carbonate wherein the alkyl group contains 2 to 10 carbon atoms.

2. The process of claim 1 further characterized in that the unsaturated compound is decene-5 and the resultant hydroformylation product is undecanol-1.

3. The process of claim 1 further characterized in that the unsaturated compound is tetradecene-7 and the resultant hydroformylation product is pentadecanol-1.

4. The process of claim 1 further characterized in that the unsaturated compound is heptene-3 and the resultant hydroformylation product is octanol-1.

5. The process of claim 1 further characterized in that the unsaturated compound is pentene-2 and the resultant hydroformylation product is hexanol-1.

6. The process of claim 1 further characterized in that the unsaturated compound is hexadecene-8 and the resultant hydroformylation product is heptadecanal-1.

7. The process of claim 1 further characterized in that the unsaturated compound is a mixture of internal olefins and the resultant hydroformylation product is a mixture of primary alcohols.

8. The process of claim 7 further characterized in that the mixture of internal olefins comprises undecene-5, dodecene-4, tridecene-6 and tetradecene-4 and the resultant mixture of primary alcohols comprises dodecanol-1, 2-methylundecanol-1, 2-ethyldecanol-1, 2-propylnonanol-1, tridecanol-1, 2-methyldodecanol-1, 2-ethylundecanol-1, tetradecanol-1, 2-methyltridecanol-1, 2-ethyldodecanol-1, pentadecanol-1, 2-methyltetradecanol-1 and 2-ethyltridecanol-1.

9. The process of claim 1 further characterized in that the ester of carbonic acid is ethylene carbonate.

10. The process of claim 1 further characterized in that the ester of carbonic acid is diethyl carbonate.

11. The process of claim 1 further characterized in that the ester of carbonic acid is diphenyl carbonate.

12. The process of claim 1 further characterized in that the ester of carbonic acid is dioctyl carbonate.

13. The process of claim 1 further characterized in that the ester of carbonic acid is octyl pentyl carbonate.

* * * * *